United States Patent [19]

Jameson et al.

[11] Patent Number: 5,227,308
[45] Date of Patent: Jul. 13, 1993

[54] METHOD FOR ASSESSING LUNG MATURITY USING FLUORESCENCE FROM NAPHTHALENE-BASED PROBES

[75] Inventors: David M. Jameson, Kailua; Nadhipuram V. Bhagavan, Honolulu, both of Hi.

[73] Assignee: University of Hawaii, Honolulu, Hi.

[21] Appl. No.: 788,291

[22] Filed: Nov. 5, 1991

[51] Int. Cl.$^5$ .............................................. G01N 21/77
[52] U.S. Cl. ..................................... 436/172; 436/907; 356/318; 250/362; 250/459.1; 128/665
[58] Field of Search ......................... 436/63, 172, 907; 356/317, 318, 417; 250/362, 459.1, 461.2; 128/665

[56] References Cited

U.S. PATENT DOCUMENTS

| | | | |
|---|---|---|---|
| 4,071,770 | 1/1978 | Shinitzky et al. | 250/461 B |
| 4,233,032 | 11/1980 | Statland et al. | 436/63 |
| 4,388,412 | 6/1983 | Yabusaki | 436/536 |
| 4,547,464 | 10/1985 | Socol | 436/2 |
| 4,784,945 | 11/1988 | Artiss et al. | 436/907 X |
| 4,784,961 | 11/1988 | Russell | 436/63 |
| 4,820,628 | 4/1989 | Weitz | 435/4 |
| 5,010,016 | 4/1991 | Sbarra | 436/907 X |

FOREIGN PATENT DOCUMENTS 1057015 11/1983 U.S.S.R. ............... 436/907

OTHER PUBLICATIONS

Parasassi, T. et al., "Detection of Phospholipid Phase Separation" Journal of Biological Chemistry, vol. 259, pp. 14011–14017 (1984).
Klausner, R. et al., "Lipid Domains in Membranes" Journal of Biological Chemistry, vol. 255, pp. 1286–1295 (1980).
Hamilton, P. R. et al., 1984, Obstetrics and Gynecology 153:52–56.
Blumenfeld, T. A., et al., Am. J. Obstet. Gynecol. 130:782–787.
Parasassi, T., et al., 1990, Biophys. J. 57:1179–1186.
Parasassi, T., et al., 1991, Biophys. J. 60:179–189.
Weber, G., et al., 1979, Biochemistry 18:3075–3078.
Merlo, S., et al., (1990) Anal. Chem. 62:2728–2735.

*Primary Examiner*—James C. Housel
*Assistant Examiner*—Jeffrey R. Snay
*Attorney, Agent, or Firm*—Flehr, Hohbach, Test, Albritton & Herbert

[57] ABSTRACT

A method for assessing lung maturity in a fetus or an infant comprises adding a fluorescent dye to a pulmonary effluent, causing the dye to fluoresce by illumination with an excitation wavelength of monochromatic light, and measuring the intensity of the fluorescence at two different wavelengths. Alternatively, the method comprises sequential illumination with two different excitation wavelengths and measurement of the intensity of fluorescence caused by each excitation wavelength at a single emission wavelength.

10 Claims, 6 Drawing Sheets

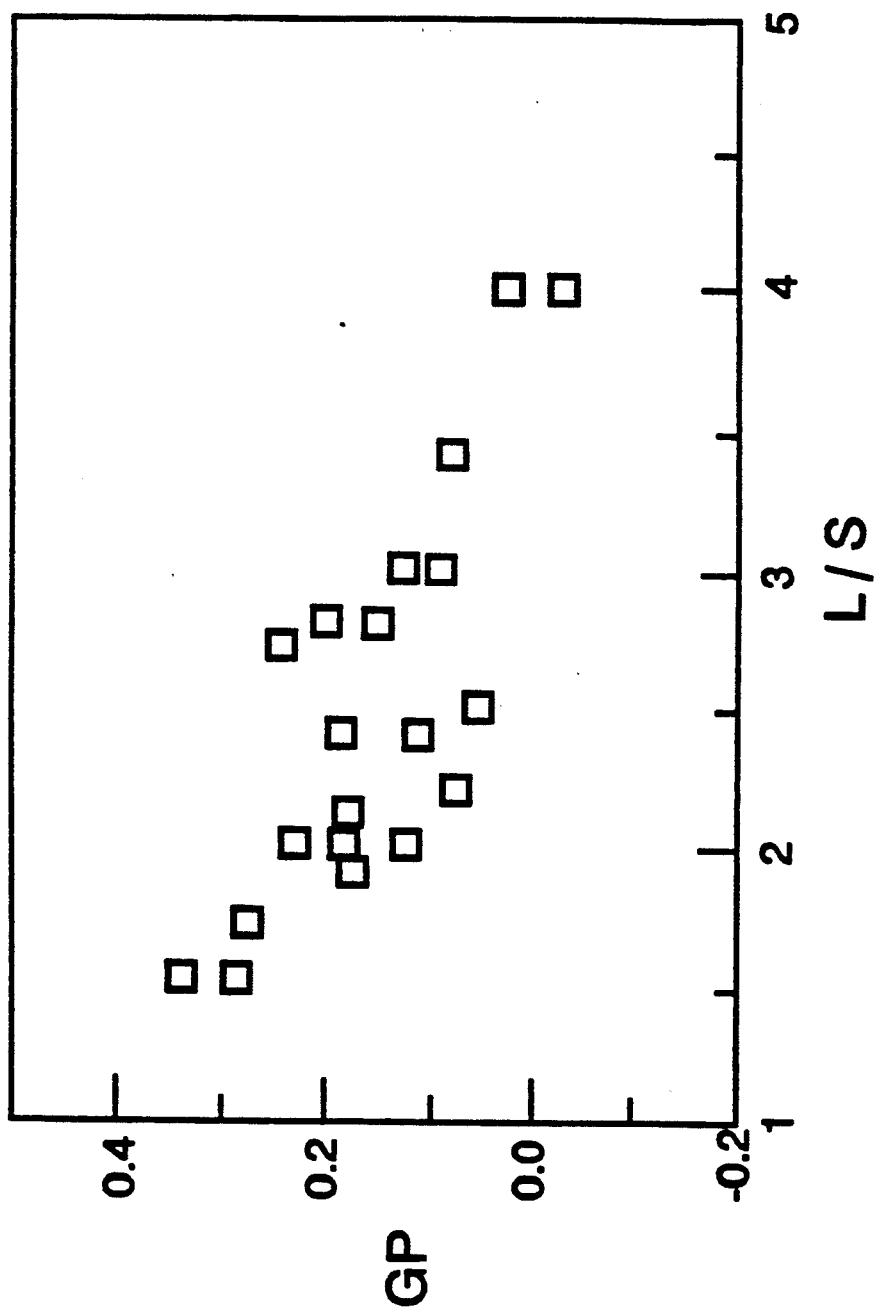

METHOD FOR ASSESSING LUNG MATURITY USING FLUORESCENCE FROM NAPHTHALENE-BASED PROBES

TECHNICAL FIELD OF THE INVENTION

This invention relates to a method for assessing lung maturity in a fetus or infant by mixing a sample containing lung fluid with a fluorescent chemical probe and measuring the generalized polarization of the fluorescence emitted by the probe.

BACKGROUND OF THE INVENTION

Respiratory distress syndrome (RDS) is one of the most critical problems associated with the clinical management of premature newborns. In the United States, about 4,000 newborns die of RDS every year. RDS is a syndrome caused by a deficiency of pulmonary surfactant, a complex mixture of phospholipids and proteins necessary for proper pulmonary function. There would be great advantages to the accurate assessment of the lung maturity of a fetus at risk for premature delivery since in many cases birth can be delayed by clinical intervention. For premature infants born with immature lungs there are treatments available such as the administration of artificial surfactant. Thus, a convenient and accurate test for fetal and/or infant lung maturity would be very valuable in the clinical management and prevention of RDS.

Amniotic fluid samples containing fetal lung effluent ay be obtained through amniocentesis or from vaginal pooling. Samples of newborn infant lung fluid may be obtained through pulmonary lavage. These samples contain pulmonary surfactant in the form of lamellar bodies, which are essentially multilaminar lipid globules. Mature pulmonary surfactant is a complex mixture of lipids and proteins with less than 5% carbohydrates. Most of the lipid is phospholipid, and the majority of that, in mature lungs, is lecithin, also known as phosphatidylcholine. The structure of lecithin is shown below:

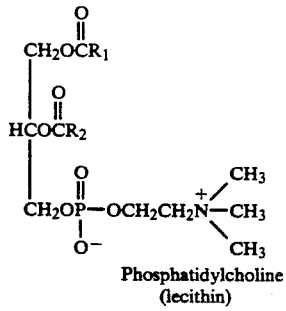

Phosphatidylcholine
(lecithin)

The R groups represent various fatty acid side chains. About 60% of the lecithin in mature surfactant has two palmitic acid side chains (dipalmitoyl lecithin).

Other lipids present in surfactant are phosphatidylglycerol, phosphatidylinositol, phosphatidylserine, phosphatidylethanolamine, and sphingomyelin. In general, the more mature the surfactant, the less viscous the lipid component thereof. Lecithin is less viscous than, for instance, sphingomyelin. As more mature surfactant is produced, the surfactant decreases in viscosity as the lecithin fraction rises in comparison to the sphingomyelin fraction. The structure of sphingomyelin is shown below:

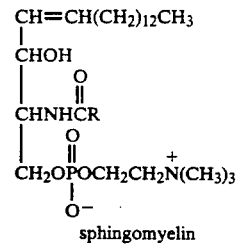

sphingomyelin

The most widely accepted measure of lung maturity is the determination of lecithin/sphingomyelin ratio (L/S ratio) in samples of amniotic fluid or infant pulmonary effluent (Hamilton, P. R. et al., 1984, *Obstetrics and Gynecology* 153:52–56). Up to 34 weeks of gestation, the L/S ratio is approximately 1, after which there is a sudden rise in lecithin concentration (Gluck, L., et al., 1971, *American J. Obstetrics and Gynecology* 109:440–445). By week 35–36 of gestation, the L/S ratio reaches approximately 4. It is commonly accepted that an L/S value of 2 or greater is an accurate indication that the fetal lung is producing sufficient surfactant to prevent RDS at birth. Conversely, however, an L/S value of less than 2 is not an accurate predictor of fetal lung immaturity (Hamilton, P. R., et al supra). Several studies have shown that as many as 77% of fetuses with L/S less than 2 have not suffered RDS upon premature birth. Nevertheless, assessment of L/S ratio is considered valuable for the prediction of lung maturity since unnecessary clinical treatment may be avoided when the L/S value is greater than 2.

The L/S ratio may be determined by the direct measurement of lecithin and sphingomyelin, most commonly by thin layer chromatography (TLC) (Bustos, R., et al., 1979, *Am. J. Obstet. Gynecol.* 133:899). TLC is limited in its clinical usefulness because the technique is labor-intensive, lengthy, and requires a specially trained technician.

An indirect measure of L/S ratio is provided by the measurement of fluorescence polarization of chemical probes added to the sample of fetal lung effluent. One such chemical probe is the fluorescent dye DPH (1.6 diphenyl-1.3.5 hexatriene) (Shinitzky, M., et al., U.S. Pat. No. 4,071,770, issued Jan. 31, 1978; Blumenfeld, T. A., et al., *Am. J. Obstet. Gynecol.* 130:782–787). Another fluorescent dye used for this purpose is NBD-PC [(7-nitro-2,1,2-benzooxadiazol-4-yl)amino]caproyl phosphatidylcholine] (Russell, J. C., U.S. Pat. No. 4,784,961, issued Nov. 15, 1988). It is generally believed that these dyes integrate into the lung fluid lipids. The mobilities of these dyes are determined by the viscosity of the lipid phase which depends upon the ratio of the various lipids. The mobility of the dye is detected by the polarization of the fluorescence of the dye after illumination by the appropriate exciting light. In samples containing a relatively viscous lipid mix (i.e. low L/S ratio), the fluorescence polarization is relatively high. Lower fluorescence polarization values are correlated with decreased lipid viscosity and with higher L/S values. It should be noted that the term "fluorescence polarization" refers to conventional polarization which is dependent on the use and measurement of polarized light; this is distinguished from the property known as "generalized polarization" which does not depend on polarized light. A disadvantage of methods dependent on fluorescent probes such as DPH and NBD-PC is that they require the use of a delicate and expensive instrument capable of producing and measuring polarized light—a fluorescence polarization photometer.

One alternative method for the assessment of lung maturity is based on the capacity of amniotic fluid to form a stable foam in the presence of an alcohol (Statland, B. E., et al, U.S. Pat. No. 4,233,032, issued Nov. 11, 1980). Another method is based on the capacity of amniotic fluid to form bubbles in an ether layer (Socol, M., U.S. Pat. No. 4,547,464, issued Oct. 15, 1985).

In addition to correlations with L/S ratio, the presence in amniotic fluid of the lipid phosphatidylglycerol has been reported to correlate with fetal lung maturity. An assay has been patented which is based on the agglutination reaction caused by the addition of an antibody to phosphatidylglycerol (Yabusaki, K. K., U.S. Pat. No. 4,388,412).

Another test is based on a change in the optical properties of an amniotic fluid sample (Weitz, S. L., U.S. Pat. No. 4,820,628, issued Apr. 11, 1989). The optical change is caused by subjecting the sample to detergent or heat, which is thought to unravel or solubilize the lamellar bodies contained therein.

Although there exist many different methods for assessing lung maturity, the value thought to correlate best with fetal lung maturity remains the L/S ratio. There remains a clear need for a quick, accurate test for L/S ratio which can be easily performed in a clinical laboratory setting.

SUMMARY AND OBJECTS OF THE INVENTION

This invention provides a method for assessing a patient's lung maturity by adding a fluorescent dye to a sample of pulmonary effluent, causing the dye to fluoresce by illumination with an excitation wavelength of monochromatic light, and measuring the intensity of the fluorescence at two different wavelengths.

The method of the invention may also be practiced by sequential illumination with two different excitation wavelengths and measurement of the intensity of fluorescence caused by each excitation wavelength at a single emission wavelength.

The fluorescent dye used in the practice of the invention is a naphthalene-based fluorophore, one example of which is Laurdan.

The measurements made in practicing the invention may be used to determine the L/S ratio or the mole-fraction of lecithin in the sample by calculation of the Generalized Polarization.

It is an object of this invention to provide a quick and accurate method for the assessment of fetal or infant lung maturity which requires only a simple instrument of measurement such as a filter fluorometer or spectrofluorometer.

BRIEF DESCRIPTION OF THE FIGURES

FIG. 4A demonstrates the relationship of GP values to L/S ratio in amniotic fluid samples.

DETAILED DESCRIPTION OF THE INVENTION

Figure 1:
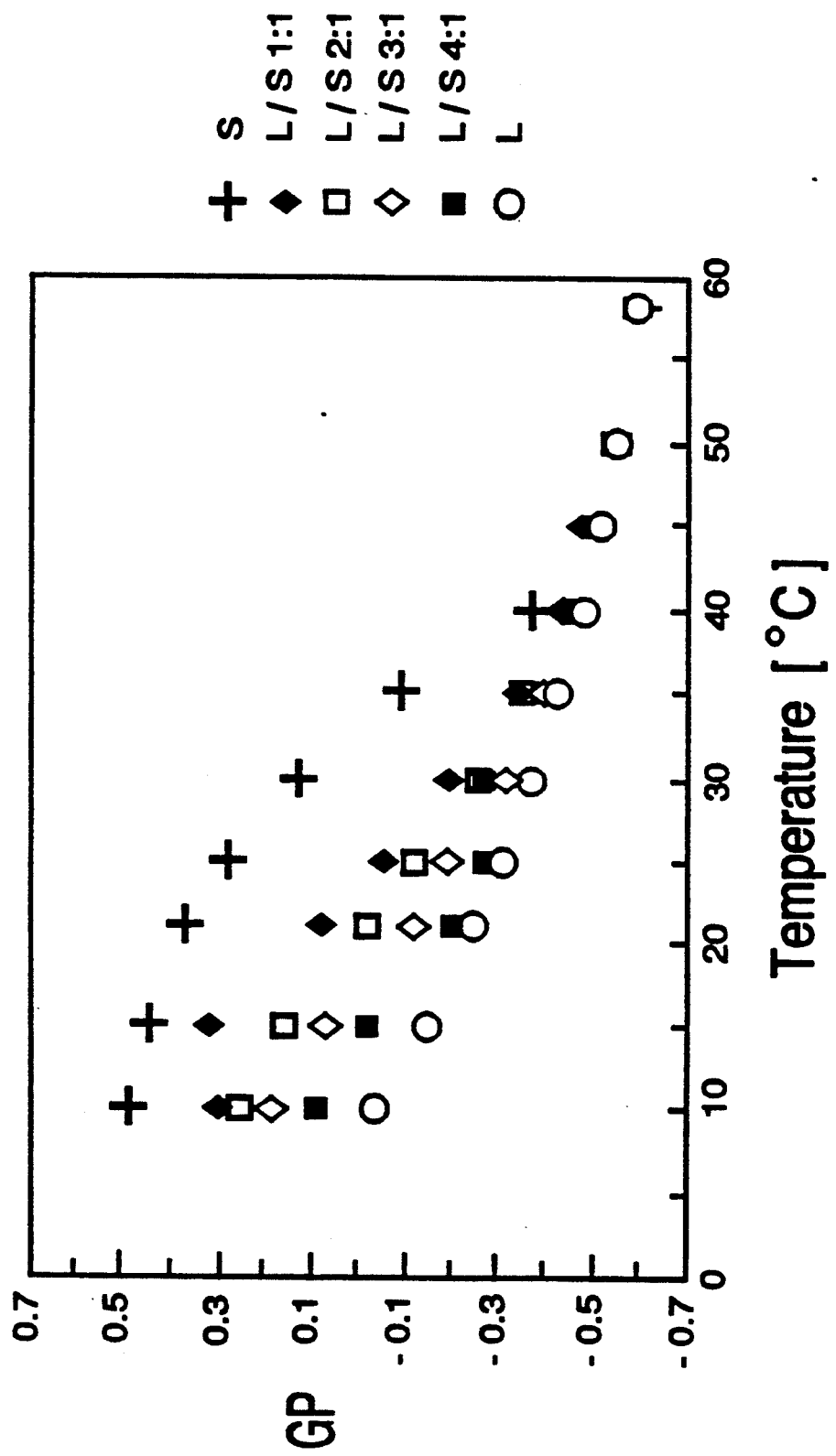
FIG. 1 shows the effect of temperature on the Generalized Polarization (GP) values obtained in vesicles prepared with a known L/S ratio.

The maturity of the lungs of a fetus or infant depends on the quality of the surfactant produced by the lungs. Surfactant is synthesized by the Type II pneumocytes in the alveolar epithelium, released into the alveolar space, and travels via the tracheal effluent into the amniotic fluid (in the case of a fetus) or into the tracheal lavage fluid (in the case of an infant being tested for lung maturity). Both amniotic fluid and tracheal lavage fluid are accessible for sampling. In general, surfactant produced by mature lungs is less viscous than that produced by immature lungs, and lower viscosity is necessary in order for the alveolar spaces to remain open. When the surfactant is of the immature type, the infant suffers from respiratory distress syndrome (RDS). The practice of this invention yields an assessment of the state of the surfactant produced by the lungs of the fetus or infant.

Children and adults may also suffer from RDS after smoke inhalation or exposure to toxic fumes. The term "assessing lung maturity" refers to a determination of the state of the surfactant produced by the lungs of a patient, without regard to the age of the patient per se.

In practicing this invention, the sample is mixed with a naphthalene-based probe, such as Laurdan, and a determination is made of a property known as Generalized Polarization (GP) caused by illumination with monochromatic light. The measurements can be made on a simple filter fluorometer or spectrofluorometer. No polarization of the illuminating light is required, nor is it necessary to assess polarization of the emitted light.

Parasassi, et al., have described the ability of Laurdan to reveal the phase state of phospholipid membranes when it is used for the determination of GP (Parasassi, T., et al., 1990, *Biophys. J.* 57:1179–1186; Parasassi, T., et al., 1991, *Biophys. J.* 60:179–189). The term "phase state" refers to the relative amount of gel phase versus liquid-crystalline phase lipid present and is loosely correlated with the viscosity of the lipid composition. An alternative naphthalene-based probe, Prodan, was described by Weber, G., et al., 1979, *Biochemistry* 18:3075–3078.

The molecular mechanism by which Laurdan or Prodan interacts with lipids is incompletely understood (Parassassi, T. et al, 1991, supra). However, the lack of such detailed knowledge does not diminish the importance of the discovery that naphthalene-based probes can act as reporters of the lipid state in amniotic fluid. In this application, the term fluorophore refers to Laurdan, Prodan, or other naphthalene-based fluorescent probes which share the properties of Laurdan described herein. Hereafter in this description, the term "Laurdan" will be used generically to refer to any such naphthalene-based probes.

In practicing the invention, the sample of amniotic fluid or lung lavage may first be mixed directly with Laurdan after light centrifugation of the fluid to remove particles. Alternatively, the lipids may be extracted from the sample with chloroform as described in Example 3. Before combining with Laurdan, the sample may be raised to a temperature of about 45° C., which is a temperature at which virtually all of the lipids are in their least viscous state. This heating step helps assure the uniform mixing and speeds the incorporation of Laurdan within the lipid components in the sample. However, when a longer incorporation time is acceptable, the invention may also be successfully practiced without heating the sample above an ambient temperature of about 20°-25° C.

It is generally believed that when Laurdan is mixed with an amniotic fluid sample, it becomes positioned within the lipid vesicles (or lamellar bodies). The polarity of the probe's environment depends upon the lipid composition. The physical basis for the measurement is the fact that the probe's absorption and emission properties depend upon the polarity of its environment. The nature of the environment near the Laurdan molecules is assessed in a measurement designated "Generalized Polarization" (GP), as defined by Parasassi, et al., 1990 and 1991, (supra). Prior to measuring the GP value, the sample containing Laurdan may be heated to a temperature approximating body temperature (i.e. about 35°-37° C.) since the phase state of lipids is affected by temperature. Raising the sample to body temperature has been found to increase the sensitivity of the assay method, however the invention may be practiced with the sample at a temperature of about 15° C. to about 40° C.

There are two alternative methods for measuring the GP value. Briefly, the first method involves illuminating the sample with one wavelength (excitation wavelength) and measuring the emission intensities at two different wavelengths. The second method involves illuminating the sample sequentially with two different excitation wavelengths and measuring the two resulting emission intensities at a single wavelength.

In measuring the GP value using the first method, the sample mixed with Laurdan is illuminated with monochromatic light of a wavelength designated A. Wavelength A is preferably in the range of about 320 nm to 440 nm, most preferably about 360 nm to 390 nm.

The intensity of emission of fluorescence is then measured on a spectrofluorometer at two different wavelengths, designated B and C. Typically, B is that emission wavelength which would yield the highest intensity if the lipid composition of the sample were in its most viscous (i.e. gel-like) state. Wavelength B is preferably in the range of about 390 nm to 470 nm, most preferably about 420 nm to 450 nm. Wavelength C is that emission wavelength which would yield the highest intensity if the lipid composition of the sample were in its least viscous (i.e. most liquid crystalline) state. Wavelength C is preferably in the range of about 470 nm to 540 nm, most preferably about 490 nm to 510 nm. Typically, the lipid composition of a given sample is in a phase state which lies between that of a gel and a liquid-crystal, thus the measured intensity values report on the actual phase state of the combined lipids in the sample.

In reference to the first method, the term "$I_B$" is defined as the intensity of emission at wavelength B, and the term "$I_C$" is defined as the intensity of emission at wavelength C. The intensity values, $I_B$ and $I_C$, may be used to calculate Generalized Polarization (GP). The GP value may then be compared to a single standard curve to obtain the L/S ratio for the sample as illustrated in FIG. 4A. Generalized Polarization is calculated according to the following formula:

$$GP = (I_B - I_C)/(I_B + I_C)$$

In the clinical setting, emission intensity values, $I_B$ and $I_C$, may also be utilized directly to estimate the L/S ratio in the sample. For instance, from precalculated GP values, a standard curve "wheel" may be prepared correlating intensity values $I_B$ and $I_C$ with known L/S ratios. L/S ratios for construction of a standard curve may be determined directly by thin layer chromatography (Bustos, R., et al., supra). It will be apparent to one of ordinary skill in the art that a single standard curve may be sufficient for all ensuing tests provided the same conditions are used in GP measurement (i.e. the same instrument settings, blanks, and the like).

A GP value may also be obtained by the second method of practicing the invention. In this method, the sample is prepared identically, but it is illuminated sequentially by monochromatic light at two different wavelengths, i.e. two different excitation wavelengths designated A and C. Wavelength A is preferably in the range of about 320 nm to 380 nm, most preferably about 340 nm to 360 nm. Wavelength C is preferably in the range of about 380 nm to 440 nm, most preferably about 400 nm to 420 nm.

The emission intensity resulting from both A and C is measured sequentially at a single wavelength B. Emission wavelength B is preferably in the range of about 460 nm to 540 nm, most preferably about 490 nm to 510 nm. In reference to this method of GP measurement (i.e. the second method) the resulting intensity values are designated $I_A$ (emission intensity resulting from excitation wavelength A) and $I_C$ (emission intensity resulting from excitation wavelength C). From these intensity values, GP is calculated by the following formula:

$$GP = (I_A - I_C)/(I_A + I_C)$$

It is to be noted that the optical property defined as Generalized Polarization (GP) is distinctly different from conventional fluorescence polarization, which is the property exploited in the methods of Shinitzky, et al. supra, and Russell supra utilizing the probes DPH and NBD-PC. The Shinitzky and Russell methods both require that the labeled sample be irradiated with polarized light and that the polarization of the emission be measured. In contrast, the measurement of GP does not require polarization of excitatory light or measurement of any direction of emitted light. The two concepts, conventional polarization versus GP, are qualitatively different. The theoretical basis for GP is described in Parassassi, et al, 1990 and 1991, supra. Moreover, since GP does not require polarized light, the instrumentation required is qualitatively different and much simpler. GP can be measured on a simple filter fluorometer or spectrofluorometer, which could result in substantial savings in initial instrument cost as well as in maintenance and replacement of the instrument. This invention should make economically feasible the assessment of fetal or infant lung maturity in small or rural clinical settings.

The following examples are offered by way of illustration and not by way of limitation.

EXAMPLE 1

This example describes the establishment of working conditions for the assessment of generalized polarization (GP) in Laurdan labeled vesicles of known lipid composition.

For preparation of multilamellar lecithin/sphingomyelin vesicles, lipids were obtained from Avanti Polar Lipids, Inc., Pelham, Ala. The lecithin reagent was L-a-lecithin (egg phosphatidylcholine) in which the fatty acid chains were 33% palmitic, 13% linoleic, 14% steric, and 32% oleic. The transition temperature of L-a-lecithin was $-10°$ C. to $-15°$ C. The sphingomyelin was derived from bovine brain. Starting solutions of lipids were made up in 99.9% methanol to make stock solutions of 2.1 mM lecithin and of 2.2 mM sphingomyelin. Samples of a final concentration of 0.1 mM lipid were made up of sphingomyelin alone, lecithin alone, and lecithin plus sphingomyelin in the ratios of 1:1, 2:1, 3:1, and 4:1 (mole:mole). The samples of methanolic lipid solutions were evaporated under $N_2$ and resuspended in 3 ml phosphate buffered saline (PBS), pH 7.4. The fluorescent probe was made into a stock solution of mM 6-dodecanoyl-2-dimethylaminonaphthalene (Laurdan) in dimethylsulfoxide (DMSO). Laurdan was obtained from Molecular Probes, Inc. (Eugene, Oreg.). Laurdan was added to each lipid sample to a final concentration of 0.5 uM, bringing the molar ratio of probe:-lipid to 1:200. The samples were then heated to 40°–45° C. and vortexed for 2 cycles of 30 seconds each.

For measurement of generalized polarization, a spectrofluorometer was used (either a model K2 spectrofluorometer from I.S.S., Inc., Champaign, Ill., or a model 8000 spectrofluorometer from SLM-Aminco, Inc., Urbana, Ill.). The excitation wavelength was 390 nm. Emission intensities were measured at 440 nm and at 490 nm for each sample at temperatures between 10° C. and 60° C. as shown in FIG. 1. Generalized polarization for each set of measurements was calculated using the formula $$GP = (I_g - I_{lc})/(I_g + I_{lc})$$

wherein $I_g$ is the emission intensity at 440 nm, which is the wavelength at which the gel phase exhibits maximum intensity, and $I_{lc}$ is the emission intensity at 490 nm, which is the wavelength at which the liquid-crystalline phase exhibits maximum emission intensity.

Results: As shown in FIG. 1, between the temperatures of 10° C. and 30° C., pure sphingomyelin and pure lecithin were distinguishable by a spread of between 0.5 and 0.6 GP units. The GP values of various ratios of lecithin:sphingomyelin were well spread between the two pure samples at these temperatures, indicating that GP could be used to determine L/S ratio in an unknown sample.

Figure 2:
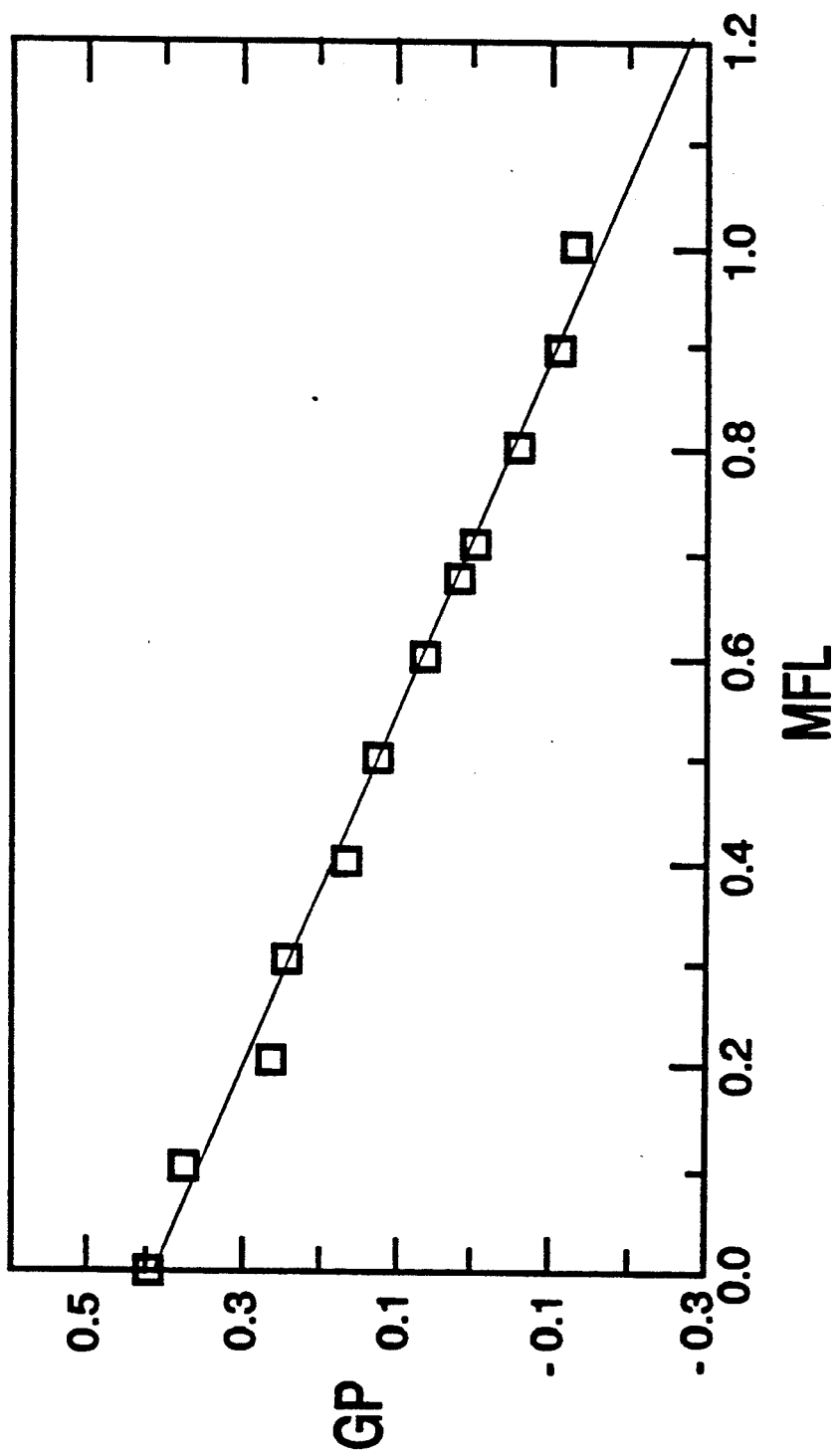
FIG. 2 shows GP values obtained at 20° C. in vesicles prepared with a known L/S ratio, which is expressed as Mole Fraction Lecithin (MFL).

FIG. 2 shows the results of a second experiment conducted at 20° C. The lipid samples were prepared essentially as described above, with the exception that 90% ethanol was used in place of methanol to dissolve the lipids initially. After the evaporation step, the gel-like residue was dissolved in a final volume of 4 ml PBS. For GP measurement, 2 ml of each sample was combined with 2 ul of a 1 mM Laurdan stock solution. The final lipid concentration in each sample was 0.15 mM; the final probe concentration was 1 uM (probe:-lipid = 1:150). GP measurements were performed at excitation wavelength = 390 nm and at emission wavelengths of 440 nm and 490 nm as above. The ratio of lecithin to sphingomyelin was expressed as the molar fraction of lecithin (MFL) calculated by the formulae $$\frac{X_s}{X_l + X_s} = MFS$$

$$1 - MFS = MFL$$

wherein $X_s$ = moles sphingomyelin, $X_l$ = moles lecithin, and MFS = mole fraction sphingomyelin. As an approximate molecular weight for lecithin, the molecular weight of dipalmitoylphosphatidylcholine was used (734 g/M). The molecular weight of sphingomyelin is 738 g/M. Thus, an MFL value of 0 indicates all sphingomyelin, a MFL of 0.67 indicates L/S = 2, and a MFL of 1.0 indicates all lecithin.

Results: As shown in FIG. 2, lower GP values correlate well with higher MFL values, indicating the usefulness of Laurdan in the assessment of lecithin:sphingomyelin ratio.

EXAMPLE 2

This example demonstrates the assessment of lecithin:sphingomyelin ratio in samples of amniotic fluid, comparing the probes Laurdan and NBD.

Amniotic fluid samples were obtained from amniocentesis procedures performed at various gestational ages at Kapiolani Medical Center, Honolulu, Hi. Each sample was lightly centrifuged and mixed with 2 ml of PBS, pH 7.4 Two milliliters of the supernatant was pipetted into a cuvette and incubated 7 minutes at 35°–40°C. Each 2 ml sample was then vortex mixed with 4 ul of a 64 uM solution of 1-palmitoyl-2,6-[(7-nitro-2,1,3-benzoxadiazol-4-yl)amino]caproyl phosphatidylcholine (NBD-PC) and 3 ul of a 1 mM Laurdan stock solution. Generalized polarization measurements were performed as described above in Example 1. Fluorescence polarization measurements were performed using polarizing optics on the same instrument at excitation wavelength 465 nm with a Schott 067 emission filter. Both measurements were performed with the samples at 20° C.

The determination of lecithin:sphingomyelin ratio (L/S) was done by the traditional thin-layer chromatography method (TLC) at the clinical laboratory of Kapiolani Medical Center. Lecithin and sphingomyelin were extracted from amniotic fluid with chloroform, precipitated with cold acetone, and redissolved in chloroform. Samples were spotted on TLC strips (Silica Gel 60F 254 pre-coated TLC roll, EM Labs, Inc., Elmford, N.J.) and lipids were separated by migration in a methanol/water/chloroform solvent.

Lipid spots on the TLC strips were stained blue through exposure to bromothymol blue dye and ammonium hydroxide fumes. The area of each spot was measured and the L/S ratio was calculated as follows:

L/S = Spot area of lecithin/Spot area of sphingomyelin

The L/S values were provided to the Applicants along with the amniotic fluid samples.

Figure 3A:
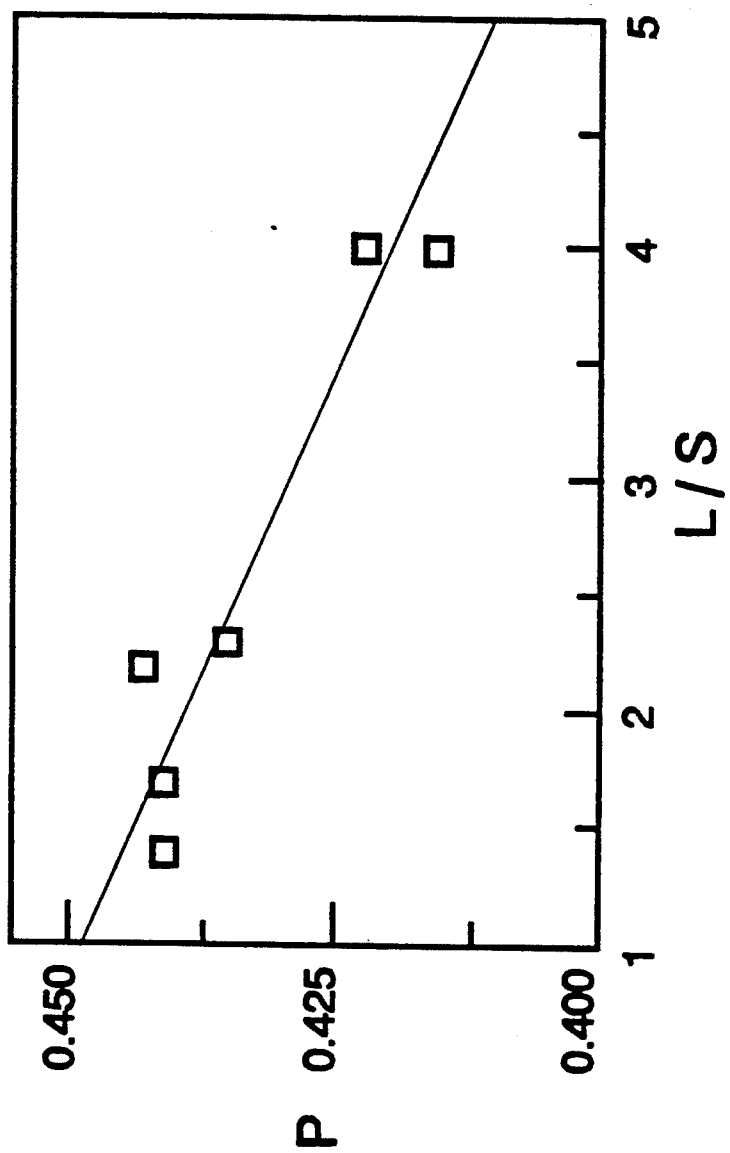
FIG. 3A shows the fluorescence polarization values obtained in amniotic fluid samples through the use of the probe NBD-PC (Russell, J. C., supra).

FIG. 3A shows the correlation of fluorescence polarization (P) of NBD-PC with L/S ratio.

Figure 3B:
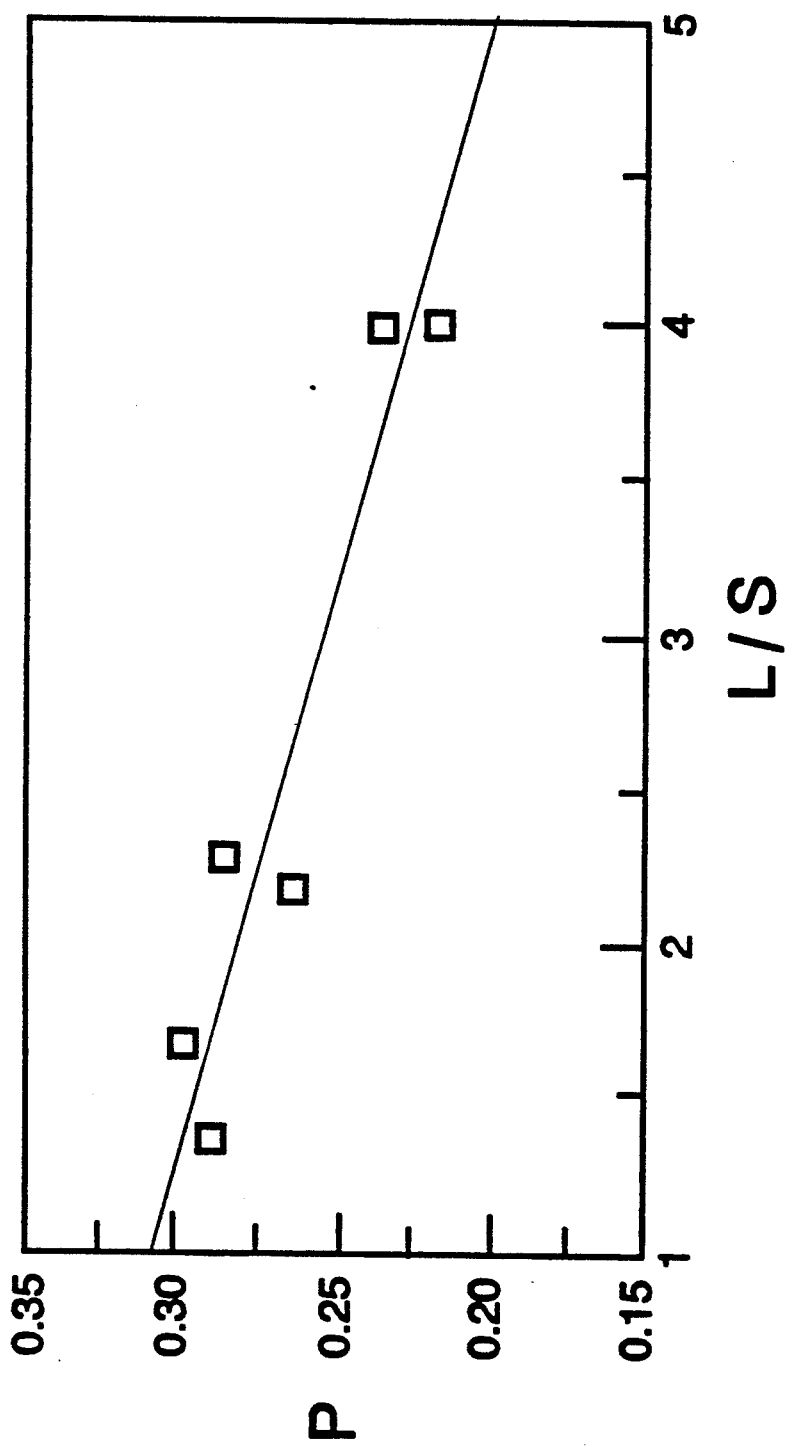
FIG. 3B shows the GP values obtained in amniotic fluid samples through the use of Laurdan.

FIG. 3B shows the correlation of GP values, reflecting GP due to the Laurdan probe in the samples, with the L/S ratio.

Conclusions: The probe Laurdan provides a method for the assessment of L/S ratio in amniotic fluid which compares favorably with the commercially used probe, NBD-PC. It should be noted that the measurement of fluorescence polarization, as required for NBD-PC, necessitates the use of a delicate and expensive instrument with polarizing optical capabilities. The probe Laurdan is advantageous over NBD-PC in that a simple filter fluorometer or spectrofluorometer is sufficient for the measurement of GP.

EXAMPLE 3

This example demonstrates the measurement of GP values in amniotic fluid samples which have been subjected to an organic phase extraction procedure.

Amniotic fluid samples, obtained as described above in Example 2, were centrifuged in a 15 ml tube at 500 g for 10 minutes at room temperature. Three milliliters of supernatant from each sample were pipetted into a 50 ml tube, to which 3 ml methanol was added and mixed well. Next, 6 ml chloroform (99 mole % pure, HPLC grade, Fischer Scientific) was added and the tubes were vortexed for 30 seconds. The tubes were then centrifuged at 500 g for 5 minutes. The lower (chloroform) phase was aspirated and transferred into a 15 ml tube and evaporated to dryness under flowing $N_2$ in a 60° C. water bath. The sides of the tubes were rinsed down with a small amount of chloroform and evaporated again as above. Each sample was brought up to a volume of 3 ml with PBS buffer, pH 7.4, warmed for 10 minutes at 40° C., and vortexed. Four microliters of 1 mM Laurdan stock solution was added to 2 ml of each sample. Generalized polarization was measured as described above, with the exception that the samples were measured at a temperature of 35° C.

Figure 4B:
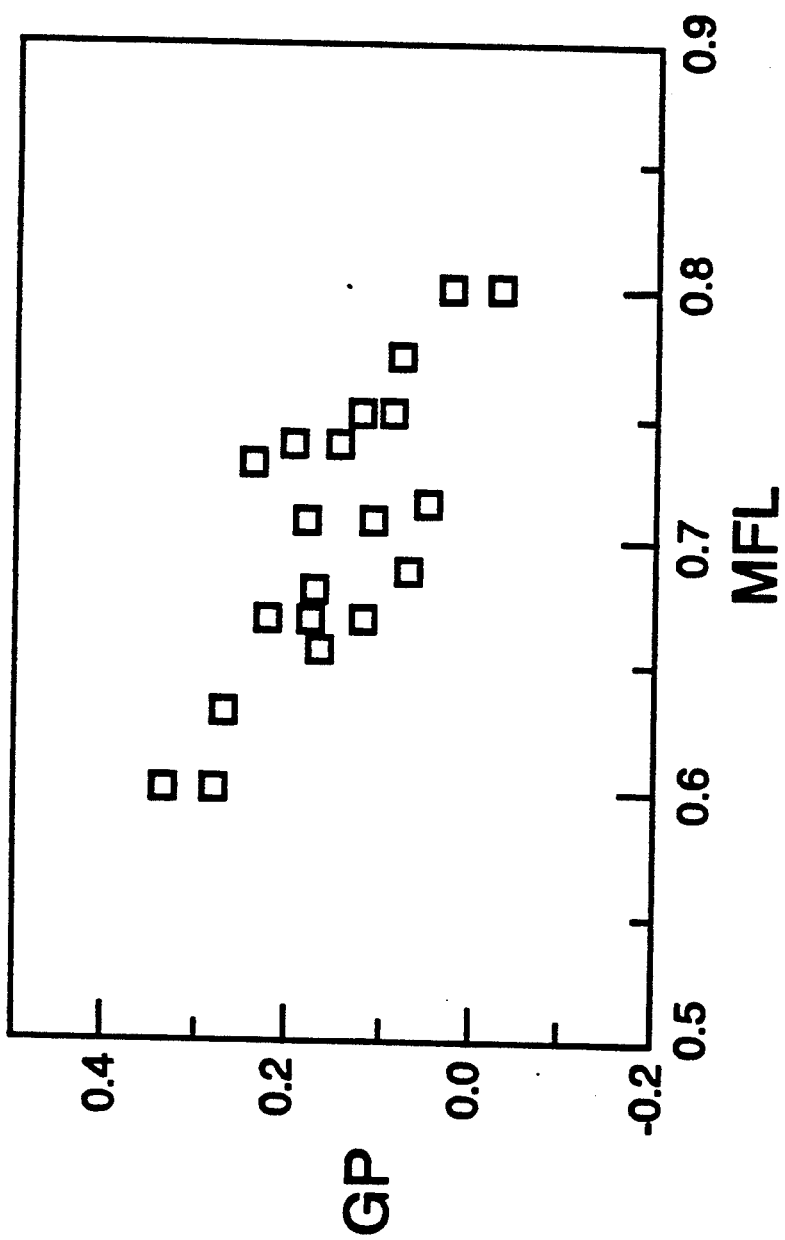
FIG. 4B shows the same data as in 4A except that the L/S ratio is expressed as Mole Fraction Lecithin (MFL).

Results: FIG. 4A shows the relationship of GP values to L/S ratio (L/S values were provided by the clinical laboratory as above). At 35° C., GP values of about 0.2 and lower correlate with L/S values of about 2.0 and greater. FIG. 4B shows the same data from the same experiment, with the exception that L/S ratio was converted to Mole Fraction Lecithin (MFL) using the formulae described in Example 1.

Conclusions: GP measurements can be used to assess the L/S ratio in amniotic fluid, and thus predict fetal lung maturity using the generally accepted rule that L/S>2 indicates maturity. Organic phase extraction of amniotic fluid prior to addition of the Laurdan probe may contribute to the sensitivity of this assay.

What is claimed is:

1. A method for assessing lung maturity in a patient comprising
   (a) adding a naphthalene-based fluorophore to a sample comprising lipids, said lipids originating from at least one lung of said patient,
   (b) illuminating said sample containing said fluorophore with monochromatic light of wavelength A to cause fluorescence,
   (c) measuring the intensity of emission of said fluorescence at wavelength B and at wavelength C to obtain the intensity values $I_B$ and $I_C$ and
   (d) using said values $I_B$ and $I_C$ to assess lung maturity wherein wavelength A is selected from 320 to 440 nm, wavelength B corresponds to the emission wavelength which would yield about the maximum intensity if the lipid composition were in its most viscous state and wavelength C corresponds to the emission wavelength which would yield about the maximum intensity if the lipid composition were in its least viscous state.

2. The method of claim 1 wherein said wavelength A is 360 nm, said wavelength B is 440 nm, and said wavelength C is 490 nm.

3. The method of claim 1 wherein said step of using said values $I_B$ and $I_C$ comprises using said measured values $I_B$ and $I_C$ to obtain the Generalized Polarization value.

4. The method of claim 1 wherein said step of using said values of $I_B$ and $I_C$ comprises using said values $I_B$ and $I_C$ to determine the mole-fraction of lecithin in said sample.

5. The method of claim 1 or claim 4 wherein said fluorophore is 6-dodecanoyl-2-dimethylaminonaphthalene.

6. The method of claim 1 or 4 wherein said patient is a fetus and said sample is obtained from the amniotic fluid surrounding said fetus.

7. The method of claim 1 or 4 wherein said patient is an infant and said sample is obtained from pulmonary effluent from said infant.

8. A method for assessing lung maturity in a patient comprising
   (a) adding a naphthalene-based fluorophore to a sample comprising lipids, said lipids originating from at least one lung of said patient,
   (b) illuminating said sample containing said fluorophore with monochromatic light of wavelength A to cause fluorescence,
   (c) measuring the intensity at wavelength B of emission of said fluorescence caused by step (b) to obtain the intensity value $I_A$
   (d) illuminating said sample containing said fluorophore with monochromatic light of wavelength C to cause fluorescence,
   (e) measuring the intensity at wavelength B of emission of said fluorescence caused by step (d) to obtain the intensity value $I_C$ and
   (f) using said values $I_A$ and $I_C$ to assess lung maturity wherein said wavelength A is selected from 320 to 380 nm, wavelength B is selected from 460 to 540 nm and wavelength C is selected from 380 to 440 nm.

9. The method of claim 8 wherein said step of using said values of $I_A$ and $I_C$ comprises using said values $I_A$ and $I_C$ to determine the mole-fraction of lecithin in said sample.

10. The method of claim 8 wherein said step of using said values of $I_A$ and $I_C$ comprises using said measured values $I_A$ and $I_C$ to obtain the Generalized Polarization value.

* * * * *